(12) United States Patent
Sen

(10) Patent No.: US 10,532,336 B2
(45) Date of Patent: Jan. 14, 2020

(54) SYSTEM FOR ANALYSIS AND REUSE OF WASTE LIQUIDS

(71) Applicant: OZBEKOGLUTH. IHC. INS. MUH. LTD. STI., Diken Ankara (TR)

(72) Inventor: Mustafa Sen, Dikmen Ankara (TR)

(73) Assignee: OZBEKOGLU ITH. IHC. INS. MUH. LTD. STI., Dikmen Ankara (TR)

(*) Notice: Subject to any disclaimer, the term of this patent is extended or adjusted under 35 U.S.C. 154(b) by 104 days.

(21) Appl. No.: 15/503,281

(22) PCT Filed: Aug. 10, 2015

(86) PCT No.: PCT/TR2015/000280
§ 371 (c)(1),
(2) Date: Feb. 10, 2017

(87) PCT Pub. No.: WO2016/024925
PCT Pub. Date: Feb. 18, 2016

(65) Prior Publication Data
US 2017/0333858 A1    Nov. 23, 2017

(30) Foreign Application Priority Data
Aug. 13, 2014    (TR) .................................. 2014/09453

(51) Int. Cl.
*B01F 15/04*    (2006.01)
*B01F 15/00*    (2006.01)
*G01N 21/85*    (2006.01)
*B01F 3/08*    (2006.01)
*B01F 3/00*    (2006.01)

(52) U.S. Cl.
CPC ........ *B01F 15/0408* (2013.01); *B01F 3/0853* (2013.01); *B01F 15/00233* (2013.01); *B01F 15/00292* (2013.01); *G01N 21/8507* (2013.01); *B01F 2003/0028* (2013.01); *B01F 2003/0896* (2013.01); *B01F 2215/0052* (2013.01)

(58) Field of Classification Search
CPC .......... B01F 15/00233; B01F 15/00292; B01F 15/0408; B01F 2003/0028; B01F 2003/0896; B01F 2215/0052; B01F 3/0853; C02F 2209/01; G01N 21/8507
USPC .......................................... 366/151.1–152.5
See application file for complete search history.

(56) References Cited

U.S. PATENT DOCUMENTS 3,591,147 A * 7/1971 Anderson ......... B01F 15/00233
366/136
4,154,537 A * 5/1979 Kress ................ B01F 15/00233
134/34

(Continued)

FOREIGN PATENT DOCUMENTS

EP          2 468 390        6/2012
WO     WO 2006/008472      1/2006

*Primary Examiner* — Tony G Soohoo
(74) *Attorney, Agent, or Firm* — Cozen O'Connor

(57) ABSTRACT

A system for measurement of quantity (density) of particles/solid materials in wastewater, and dilution of particle quantity based on the intended application. Currently enabling quick and serial measurement of particle quantity in laboratory environment, this system is placed inside the desired step of the process of an industrial facility. This way, the system yields quick results and in turn reduces the analysis and evaluation costs.

2 Claims, 3 Drawing Sheets

(56) References Cited

U.S. PATENT DOCUMENTS

| | | | | |
|---|---|---|---|---|
| 4,474,476 A | * | 10/1984 | Thomsen | B41F 33/0054 |
| | | | | 101/451 |
| 4,654,802 A | * | 3/1987 | Davis | B01F 15/00233 |
| | | | | 137/3 |
| 4,764,019 A | * | 8/1988 | Kaminski | B01F 3/1271 |
| | | | | 366/136 |
| 4,863,277 A | * | 9/1989 | Neal | B01F 3/1271 |
| | | | | 366/137 |
| 5,027,267 A | * | 6/1991 | Pitts | B01F 3/1271 |
| | | | | 366/152.1 |
| 5,103,908 A | * | 4/1992 | Allen | B01F 3/04836 |
| | | | | 166/285 |
| 5,190,374 A | * | 3/1993 | Harms | B01F 5/205 |
| | | | | 366/165.2 |
| 5,281,023 A | * | 1/1994 | Cedillo | B01F 15/00155 |
| | | | | 366/152.1 |
| 5,452,954 A | * | 9/1995 | Handke | B28C 7/02 |
| | | | | 137/4 |
| 5,503,473 A | * | 4/1996 | Dearing, Sr. | B01F 15/00155 |
| | | | | 366/152.2 |
| 5,571,281 A | * | 11/1996 | Allen | B01F 3/12 |
| | | | | 366/163.1 |
| 5,573,333 A | * | 11/1996 | Dahlman | B01F 15/00136 |
| | | | | 137/4 |
| 6,496,781 B1 | | 12/2002 | Chen | |
| 6,923,568 B2 | * | 8/2005 | Wilmer | B01F 5/0451 |
| | | | | 366/152.1 |
| 7,353,874 B2 | * | 4/2008 | Dykstra | B01F 13/1013 |
| | | | | 137/88 |
| 7,470,365 B2 | * | 12/2008 | Hong | C02F 1/5209 |
| | | | | 210/202 |
| 7,494,263 B2 | * | 2/2009 | Dykstra | B01F 15/00207 |
| | | | | 137/88 |
| 7,543,645 B2 | * | 6/2009 | Dykstra | B01F 13/1013 |
| | | | | 137/88 |
| 7,561,943 B2 | * | 7/2009 | Dykstra | G05D 11/133 |
| | | | | 166/285 |
| 7,567,856 B2 | * | 7/2009 | Dykstra | G05D 11/133 |
| | | | | 166/285 |
| 7,600,414 B2 | * | 10/2009 | Allen | G01N 9/00 |
| | | | | 73/32 R |
| 7,905,653 B2 | * | 3/2011 | Wilmer | B01F 3/0861 |
| | | | | 366/132 |
| 8,177,411 B2 | * | 5/2012 | Borgstadt | B01F 13/1013 |
| | | | | 366/15 |
| 9,695,670 B2 | * | 7/2017 | Ayo | E21B 33/13 |
| 2004/0057334 A1 | | 3/2004 | Wilmer | |
| 2007/0109912 A1 | * | 5/2007 | Urquhart | B24B 57/00 |
| | | | | 366/136 |
| 2014/0014588 A1 | * | 1/2014 | Koehorst | C02F 1/008 |
| | | | | 210/709 |
| 2014/0044485 A1 | * | 2/2014 | Wallace | C09K 17/06 |
| | | | | 405/36 |
| 2014/0340980 A1 | * | 11/2014 | Brandt | B01F 15/0408 |
| | | | | 366/152.4 |
| 2015/0298082 A1 | * | 10/2015 | Machuca | B01F 15/0022 |
| | | | | 366/152.3 |
| 2016/0090512 A1 | * | 3/2016 | Humphreys | B01F 5/106 |
| | | | | 118/698 |
| 2017/0333858 A1 | * | 11/2017 | Sen | B01F 15/00233 |

\* cited by examiner

SYSTEM FOR ANALYSIS AND REUSE OF WASTE LIQUIDS

PRIORITY CLAIM

This is a U.S. national stage of application No. PCT/TR2015/000280, filed on Aug. 10, 2015. Priority is claimed on Turkish Application No. TR 2014/09453 filed Aug. 13, 2014, the content of which is incorporated here by reference.

BACKGROUND OF THE INVENTION

1. Field of the Invention

The invention is related to a system for measurement of quantity (density) of particles/solid materials in wastewater, and dilution of particle quantity based on the intended application. Currently enabling quick and serial measurement of particle quantity in laboratory environment, this system is placed inside the desired step of the process of an industrial facility. This way, the system yields quick results and in turn reduces the analysis and evaluation costs.

DISCUSSION OF THE RELATED ART

With the increasing environmental awareness, the grey water, also called wastewater, is now being treated and used in numerous fields across the industry with releasing to the nature as pollutants.

However; the use of water which contain large quantities of heavy metal slurry or unwanted particles in such industries in an uncontrolled way and without treatment may cause environmental pollution, decrease in quality of ecosystem around the area of use or health issues depending on the industrial area of use.

As a matter of fact, wastewater-using industrial fields need specific quality requirements. Therefore, the water obtained from the grey water recycling system should conform to the standards of the intended area of use. Generally, the utility water obtained via treating grey water must be hygienically and microbiologically safe, colorless and totally free from solid wastes. No odor must form a few days after the treated water is stored. Currently, due to lack of legal regulations on quality of utility water and on working principles of enterprises, it is recommended to ask a written guarantee for the quality of grey water treated from the companies manufacturing grey water recycling system.

Because grey water contains numerous components such as $SiO_2$, $P_2O_5$, $Fe_2O_3$, CaO, $Al_2O_3$, MgO, ZnO, TiO2, grid and sieving, sedimentation pond or neutralization, coagulation and flocculation and similar methods are employed in making use of such waters.

For the processes of treatment, impurification and making clean as desired used at the industrial facilities; first of all, it is necessary to calculate the ratio of pollutants or unwanted particles in the grey water. In order to determine ratio of unwanted particles in the liquid, to make the liquid reusable again and introduce to the production process again, the entire production system is paused and water samples are analyzed in the laboratory in the current state of technique. Since it takes hours and sometimes days to get the analysis results, it costs a lot for the industry to pause the process. For reasons of such disadvantages, it becomes difficult to reach a certain standard in use of grey waters and particles in undesired level remain in the water.

An example of the current state of the technique is the patent application numbered WO2006008472 A2. This application titled grey water filtering system describes a filtering assembly used for recycling of grey water. This system uses a filter for filtering the unwanted materials in grey water which separates the particles and solid materials from water. Grey water is recycled by means of a filter mechanism which includes a support mesh or blanket holding a sedimentary material produced by electrolysis of seawater.

However, the system covered by the above-mentioned application is rather costly and time consuming. Moreover, the water undergoing these processes is not clean enough to be used as potable water and in this case, it does not make it convenient for the consumer to make use of such high-cost processes for the purpose of treating water for only industrial purposes.

SUMMARY OF THE INVENTION

A system is described, which measures, records, reports the quantity of particles in the liquid, which changes the liquid mixture ratios and which is automatically controlled by computers in order to obtain liquids containing particles in the desired levels based on the area of use of liquids and desire of user.

A further purpose of the present invention is to prevent problems experienced in obtaining grey water at various levels to be used for different industrial applications.

A further purpose of the present invention is to make sure that quantity and density of particles and solid materials in liquids are easily determined.

A further purpose of the present invention is to prevent loss of time experienced in traditional methods used for determination of material density and content.

A further purpose of the present invention is to reduce the costs associated with analysis of particles and change of particle ratios in liquids.

Figure 1:
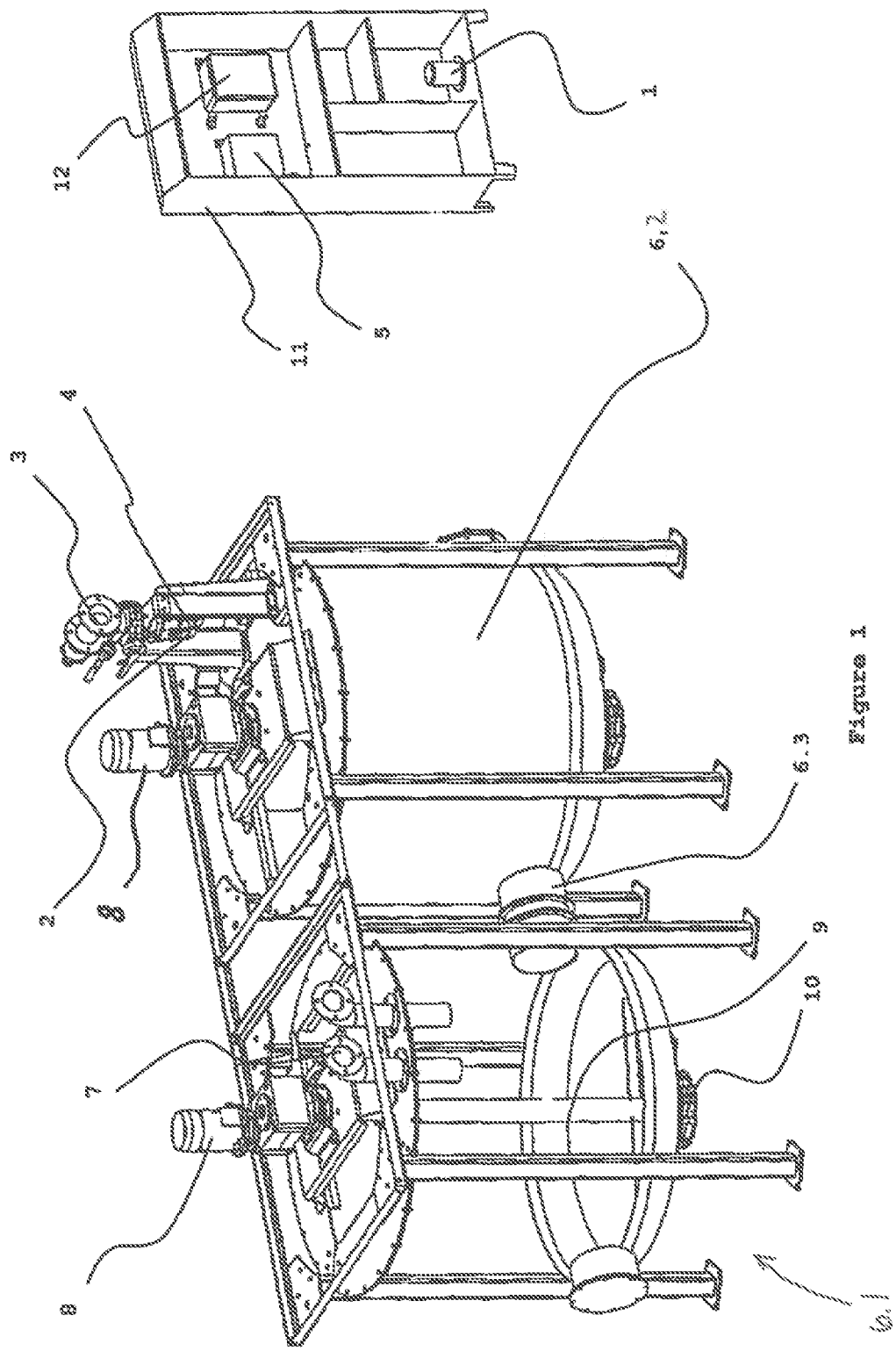
FIG. 1 is a view of wastewater reclamation system

The parts shown above have been numbered one by one and the part names corresponding to these numbers are given below;

1. Pumps for automatic water cleaning line
2. Analyses equipment cleaning line
3. Wastewater feeding line
4. Analysis equipment
    4.1. Transmitter* system
        4.1.1. transmitter probe
    4.2. Receiver system
        4.2.1. Receiver probe
5. System processor
6. Tank
    6.1. Clean water tank
    6.2. Agitation tank
    6.3. Transfer cover
7. Clean water feeding line
8. Agitator drive mechanism
9. Agitator
10. Discharge cover
11. Control panel
12. PLC/Control system

DESCRIPTION OF INVENTION

This invention relates to a system which determines the particle quantity in liquids in real-time, as seen in the embodiment of FIG. 1, which comprises a waste liquid feeding line (3) which ensures feeding waste liquid into the system; at least two tanks (6), as shown in this embodiment, a clean water tank (6.1) and a main (or agitation) tank (6.2), in which the liquid is stored and each of which comprises an agitator (9) which ensures a homogenous mixture in a way precluding sedimentation of particles and solid materials in the liquid and agitator drive mechanism (8) which controls the agitator (9). A clean water feeding line (7) provides clean water intake to the clean water tank (6.1); a discharge cover/valve (10) which ensures that the homogenized liquid and/or solid material is discharged and transmitted to the place of use; at least one analysis equipment (4) which determines the particle density of waste liquid, entering into tank, during the liquid flow; PLC/Control system (12) located on the control panel (11) to which the values received from the analysis equipment (4) are transferred; cleaning line (2) which feeds pressurized water to analysis equipment (4) by means of automatic water cleaning line pump (1).

It is aimed by using the system covered by the present invention that liquids containing particles in desired ratios can be obtained based on the place of application and user of waste liquids and for this purpose, a system, which measures, records, reports the quantity of particles in the liquid, which changes the liquid mixture ratios and which is automatically controlled by computers while the wastewater is transmitted/transported from one place to another, has been created.

The process of obtaining liquids in desired particle density in this system comprises the following steps:

Storage of wastewater in tanks (6) by passing through analysis equipment (4) received from waste liquid feeding line (3), Receipt of information concerning pollution degree of water the density of particles inside the water by analysis equipment (4) during passage of waste liquid to the tank, and transfer of signals sensed to the processor (5) and PLC control system (12) on the control panel (12), Conversion by PLC control system (12) of signal received from analysis equipment (4) into particle density and display of these values on the PLC screen, Comparison of values with density values predetermined by user and recorded in the control system database, Transfer of water in the tank outside the tank if the value measured conforms to the measurement range of density value predetermined by the user and recorded in the system, If the value measured does not conform to the measurement range of density value predetermined by the user and recorded in the system, calculation by PLC control system of amount of water necessary to increase the water amount and dilute the density and realization of water intake from clean liquid feeding line (7), Removal of final homogenized liquid from tank through discharge cover/valve (10) and transfer that liquid to place of use.

While the above-described steps are realized, the agitator (9) is simultaneously operated by agitator drive mechanism (8) in a manner that prevents sedimentation of particles in the liquid inside the tank (6) and ensures homogenous liquids. Thus, the liquid collected in the tank (6) is always homogenous.

The most prominent characteristics of the system is that there is no need to pause and interrupt the process across the industrial facility during the analyses. Instant information received and analysis results enable the continuation of process as desired. This way, more work is performed at a unit of time and expenditures made for analysis is reduced.

Since the employees conducting such analyses will not be needed any more within the system, standard quality values are yielded that do not depend on individual experience and care. This characteristic in turn allows the use of the system at any type of industrial facility safely and reliably.

Another factor in the use of the system in a safe and reliable way is that the system features self-quality control and regular self-calibration. The system feeds pressurized water to the analysis equipments (4) by means of analysis equipment cleaning line (2). The analysis equipment cleaning line (2) that feeds pressurized water is fed through automatic water cleaning pump (1). Thus, the system prevents sedimentation of unwanted particles on the analysis equipment (4) and erroneous measurements.

Probes, sensors and similar transceiver mechanisms can be used in the present system under this invention.

In this case, a further prominent characteristic of the invention is the relation between the analysis equipment (4), which can also be probe sets (4) and the PLC control system (12). The probe set (4) given in the FIG. 2 comprises transmitter system (4.1) to which the transmitter probe (4.1.1) is connected and the receiver system (4.2) to which the receive probe (4.2.1) is connected.

The probe sets (4) can vary depending on the industrial process, in which the system will be used, and may also comprise beam, magnetic field, sound and similar wave transceivers.

Figure 2:
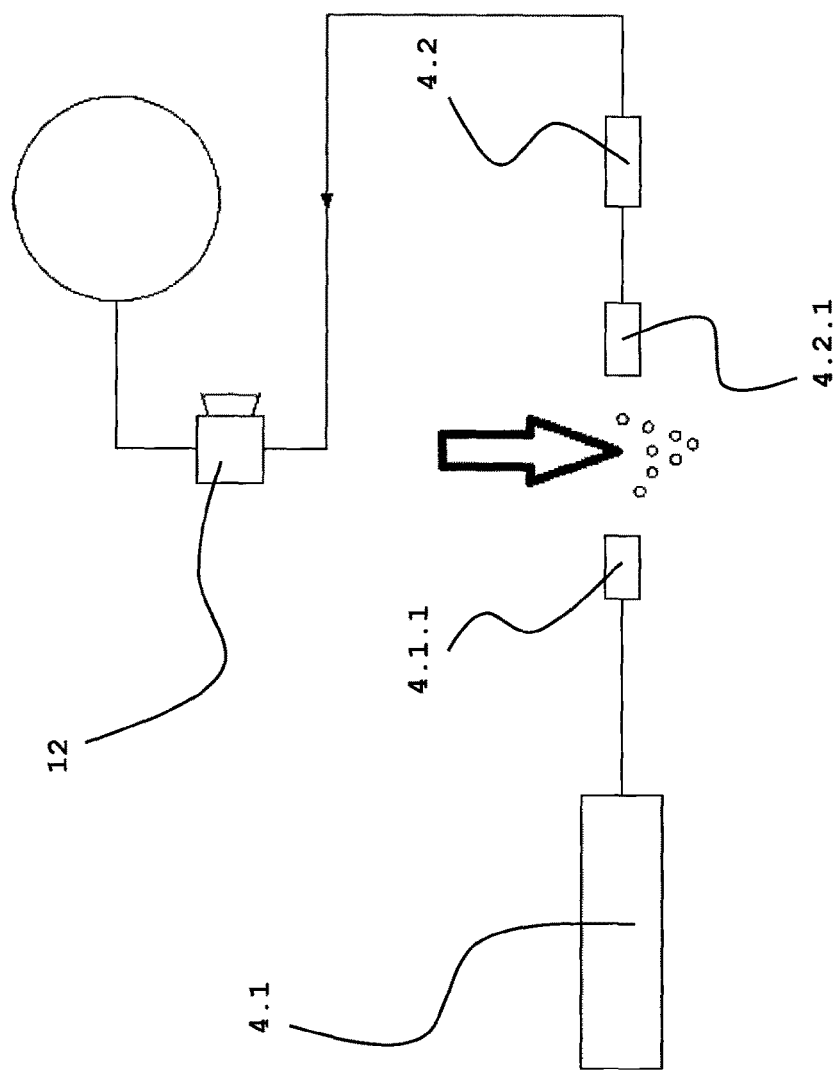
FIG. 2 is a view of particle quantity analyzer comprising probe sets and PLC system.

To illustrate, when a system using beam probes (4) is considered; the beams emitted from the transmitter probe (4.1.1) through the power supplied by transmitter system (4.1) hit the particles inside the water flow, passing through the waste liquid feeding line (3) and shown by arrow in FIG. 2, and transferred to the receiver system (4.2) by the receiver probe (4.2.1). The receiver system (4.2) transmits the signals received to the PLC and control system (12) and the process is run.

At this point, the beam transmitter system (4.1) can be selected as to send infrared, ultraviolet and similar beams.

On the other hand, the receiver probe (4.2.1) must have the capability to detect the wavelength of beams emitted from the transmitter system (4.1), to which it is connected.

Therefore, the probe sets (4) must be located inside the water flow and waste liquid feeding line (3) on the point the water flows into tank (6).

Since the waste liquid (water) flowing inside the tank is not homogenized yet, waste liquid (water) which has the same particle density should not always pass through the probe sets. However, because with the transfer of signals received from the receiver probe (4.2.1) to the PLC control system (12) the system presents the final density as the average of signals obtained during the liquid passage, the error margin decreases.

Figure 3:
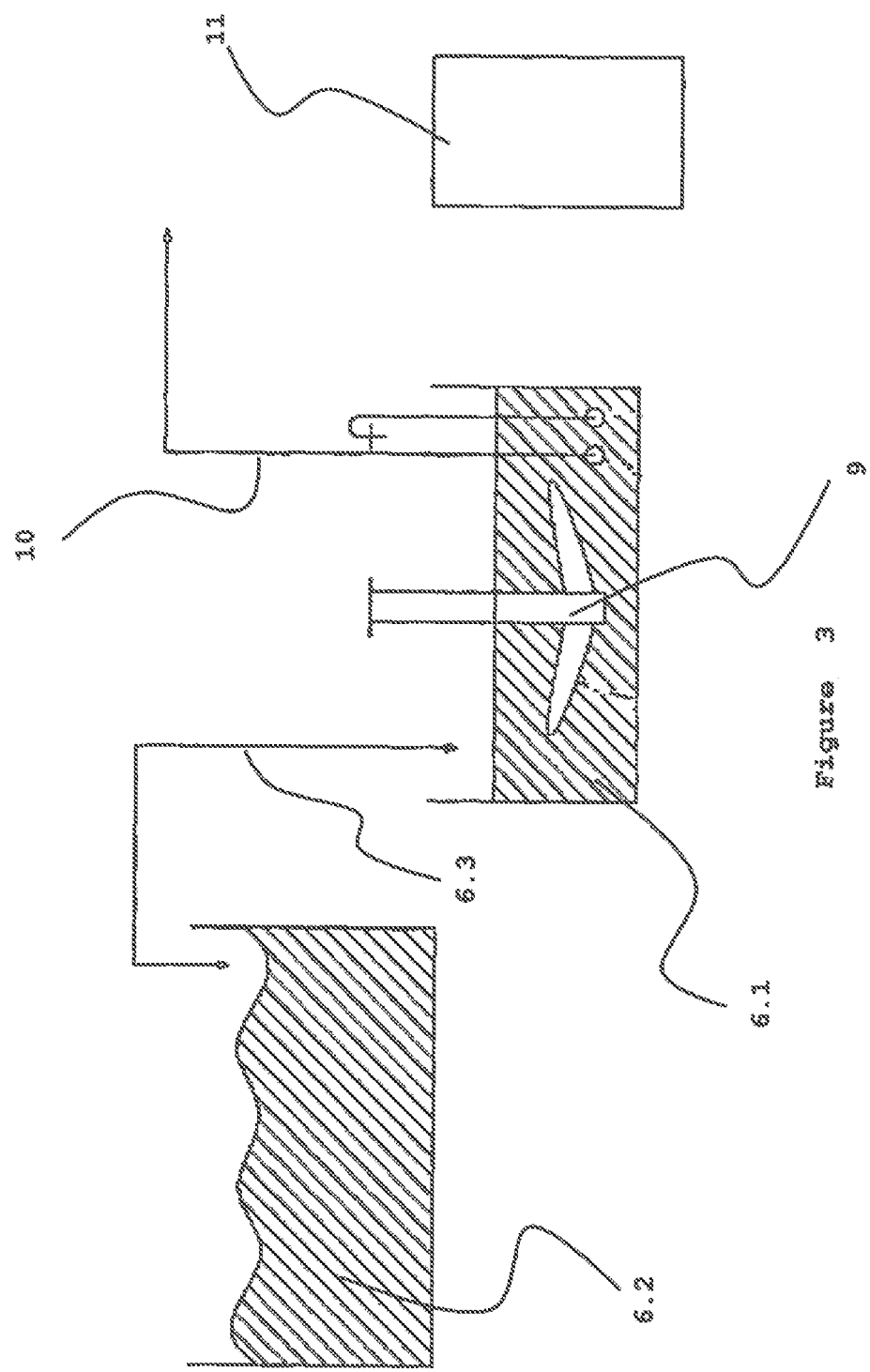
FIG. 3 is a view of station of blending water preparation and homogenization for concrete production.

Being also used for making the grey waters used in especially mortar mixing, drenching and material preparation in construction sites impurity level necessary optimum yield, the system aims at obtaining water in impurity level that can be used for mortars and other mixtures by reducing the impurities in the waters. When the subject system is detailed in a way suitable specifically for process of blend water preparation for concrete production, the system seen in FIG. 3 is obtained.

According to this, the system can have more than one tank (6). One of these tanks is a clean water tank (6.1) that stores dean water, this stored dean water is used for dilution of waste water in the main tank (6.2) when necessary. Thus, the water passage occurs between the clean water tank and the main tank (6.2), also called agitation tank, by means of transfer cover (6.3) in line with the command received from the PLC control system (12). The amount of water passing depends on the calculation made by the PLC control system (12), which determines the particle density of wastewater entering into the main tank, by comparing the densities recorded in the system database with the values measured. Note that the agitator 9 in the main tank (6.2) is not shown in FIG. 3, for simplification of the schematic view of that figure.

All the components as well as the number and dimension of such components of the system under the present invention may vary based on the industrial process, in the which the system will be used.

The invention claimed is:

1. An apparatus for measurement, at any given time, of a particle density of waste liquid flowing on a common waste liquid line and dilution of the particle density in a manner selectable, based on a usage parameter, by a PLC/control system (12), the apparatus comprising:
   a waste liquid feeding line (3) that feeds waste liquid into the apparatus;
   a main tank (6.2) in which the waste liquid fed via the waste liquid feeding line (3) is stored, the main tank (6.2) having arranged therein a first agitator (9) and a first agitator drive mechanism (8);
   a clean water tank (6.1), adjacent the main tank (6.2) in which clean water is stored, the clean water tank (6.1) having arranged therein a second agitator (9) and a second agitator drive mechanism (8); and
   a clean water feeding line (7), that provides clean water intake to the clean water tank (6.1);
   a discharge cover/valve (10) arranged at the bottom of the clean water tank (6.1), and configured to facilitate discharge and transmission of homogenized liquid and/or solid material to a place of use;
   analysis equipment (4), located in the waste liquid feeding line (3), and configured to determine the particle density of the waste liquid entering into the main tank (6.2) during liquid flow, said analysis equipment (4) comprising a transmitter system (4.1) to which a transmitter probe (4.1.1) is connected, a receiver system (4.2) to which a receiver probe (4.2.1) is connected, the analysis equipment (4) being in communication with the PLC/control system (12);
   each of the first and second agitators (9) is located, respectively, at a bottom of the main and clean water tanks (6.2, 6.1) to obtain homogenous fluids from the respective tanks; and
   an analysis equipment cleaning line (2) that feeds pressurized water to the analysis equipment (4) by an automatic water cleaning line pump (1) to clean the analysis equipment (4), the analysis equipment cleaning line (2) being located on the main tank (6.2) in a section where the waste liquid flows into the main tank (6.2) via the waste liquid feeding line (3), so that the analysis equipment can measure, at any given instant, the particle density of the waste liquid being transferred into the main tank (6.2), and transfer measurement results to the PLC/control system (12).

2. The apparatus according to claim 1, wherein the analysis equipment is located on a point at which the waste liquid feeding line flows into the main tank.

* * * * *